(12) United States Patent
Trogden et al.

(10) Patent No.: US 9,763,959 B2
(45) Date of Patent: *Sep. 19, 2017

(54) COMPOSITIONS AND METHODS FOR STIMULATING HAIR GROWTH

(71) Applicant: Allergan, Inc., Irvine, CA (US)

(72) Inventors: John T. Trogden, Villa Park, CA (US); Adnan K. Salameh, Irvine, CA (US); Chetan P. Pujara, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,273

(22) Filed: Aug. 18, 2015

(65) Prior Publication Data

US 2016/0199277 A1    Jul. 14, 2016

Related U.S. Application Data

(63) Continuation of application No. 14/163,954, filed on Jan. 24, 2014, now Pat. No. 9,138,480, which is a continuation of application No. 12/940,711, filed on Nov. 5, 2010, now abandoned.

(60) Provisional application No. 61/259,368, filed on Nov. 9, 2009.

(51) Int. Cl.
| | |
|---|---|
| *A61K 31/5575* | (2006.01) |
| *A61K 8/34* | (2006.01) |
| *A61K 8/39* | (2006.01) |
| *A61K 8/37* | (2006.01) |
| *A61K 8/36* | (2006.01) |
| *A61Q 7/00* | (2006.01) |
| *A61K 8/81* | (2006.01) |
| *A61K 8/41* | (2006.01) |
| *A61K 8/02* | (2006.01) |
| *A61K 8/86* | (2006.01) |
| *A61K 9/00* | (2006.01) |
| *A61K 9/06* | (2006.01) |
| *A61K 9/12* | (2006.01) |
| *A61K 9/14* | (2006.01) |
| *A61K 8/04* | (2006.01) |
| *A61K 8/42* | (2006.01) |
| *A61K 31/16* | (2006.01) |
| *A61K 47/08* | (2006.01) |
| *A61K 47/10* | (2017.01) |
| *A61K 47/22* | (2006.01) |

(52) U.S. Cl.
CPC ......... *A61K 31/5575* (2013.01); *A61K 8/022* (2013.01); *A61K 8/0216* (2013.01); *A61K 8/042* (2013.01); *A61K 8/046* (2013.01); *A61K 8/34* (2013.01); *A61K 8/345* (2013.01); *A61K 8/39* (2013.01); *A61K 8/41* (2013.01); *A61K 8/42* (2013.01); *A61K 8/8147* (2013.01); *A61K 8/86* (2013.01); *A61K 9/0014* (2013.01); *A61K 9/06* (2013.01); *A61K 9/12* (2013.01); *A61K 9/122* (2013.01); *A61K 9/14* (2013.01); *A61K 31/16* (2013.01); *A61K 47/08* (2013.01); *A61K 47/10* (2013.01); *A61K 47/22* (2013.01); *A61Q 7/00* (2013.01); *A61K 2800/592* (2013.01); *A61K 2800/74* (2013.01); *A61K 2800/87* (2013.01)

(58) Field of Classification Search
CPC ...... A61K 31/5575; A61K 8/34; A61K 8/345; A61K 8/361; A61K 8/375; A61K 8/39; A61Q 7/00
USPC ........ 514/573, 613, 617; 564/170, 171, 189; 424/70.1, 400, 401
See application file for complete search history.

(56) References Cited

U.S. PATENT DOCUMENTS

| 3,382,247 A | 5/1968 | Anthony et al. |
|---|---|---|
| 3,644,363 A | 2/1972 | Kim |
| 4,128,577 A | 12/1978 | Nelson |
| 4,139,619 A | 2/1979 | Chidsey, III |

(Continued)

FOREIGN PATENT DOCUMENTS

| CA | 1208560 | 7/1986 |
|---|---|---|
| CA | 2144967 | 3/1994 |

(Continued)

OTHER PUBLICATIONS

Abramovitz, Mark et al, The Utilization of Recombinant prostanoid Receptors to Determine the Affinities and Selectivities of Prostaglandins and Related Analogs, Biochimica et Biophysica Acta, 2000, 285-293, 1483.

(Continued)

*Primary Examiner* — Irina Neagu
(74) *Attorney, Agent, or Firm* — Lorenz Siddiqi

(57) ABSTRACT

Methods and compositions for stimulating the growth of hair are disclosed wherein said compositions include a cyclopentane heptanoic acid, 2-cycloalkyl or arylalkyl compound represented by the formula I

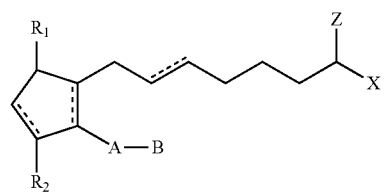

wherein the dashed bonds represent the presence or absence of a double bond which can be in the cis or trans configuration and A, B, Z, X, $R_1$ and $R_2$ are as defined in the specification and a penetration enhancer. Such compositions are used in stimulating hair growth of human or non-human animals.

10 Claims, No Drawings

(56) References Cited

U.S. PATENT DOCUMENTS

| | | |
|---|---|---|
| 4,311,707 A | 1/1982 | Birnbaum et al. |
| 4,543,353 A | 9/1985 | Faustini et al. |
| 4,596,812 A | 6/1986 | Chidsey et al. |
| 4,599,353 A | 7/1986 | Bito |
| 4,812,457 A | 3/1989 | Narumiya et al. |
| 4,839,342 A | 6/1989 | Kaswan |
| 4,883,581 A | 11/1989 | Dickakian |
| 4,888,354 A | 12/1989 | Chang et al. |
| 4,889,845 A | 12/1989 | Ritter et al. |
| 4,952,581 A | 8/1990 | Bito et al. |
| 4,968,619 A | 11/1990 | Curtiss, III |
| 4,968,812 A | 11/1990 | Wang et al. |
| 5,001,153 A | 3/1991 | Ueno et al. |
| 5,194,429 A | 3/1993 | Ueno et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,321,128 A | 6/1994 | Stjernschantz et al. |
| 5,352,708 A | 10/1994 | Woodward et al. |
| 5,422,368 A | 6/1995 | Stjernschantz et al. |
| 5,422,369 A | 6/1995 | Stjernschantz et al. |
| 5,431,881 A | 7/1995 | Palacios |
| 5,474,979 A | 12/1995 | Ding et al. |
| 5,480,900 A | 1/1996 | DeSantis et al. |
| 5,508,303 A | 4/1996 | Isogaya et al. |
| 5,510,383 A | 4/1996 | Bishop et al. |
| 5,545,655 A | 8/1996 | Friedlander et al. |
| 5,578,618 A | 11/1996 | Stjernschantz et al. |
| 5,578,643 A | 11/1996 | Hanson et al. |
| 5,607,978 A | 3/1997 | Woodward et al. |
| 5,688,819 A | 11/1997 | Woodward et al. |
| 5,698,733 A | 12/1997 | Hellberg et al. |
| 5,773,472 A | 6/1998 | Stjernschantz et al. |
| 5,789,244 A | 8/1998 | Heidrun et al. |
| 6,025,392 A | 2/2000 | Selliah et al. |
| 6,124,344 A | 9/2000 | Burk et al. |
| 6,160,129 A | 12/2000 | Burk et al. |
| 6,203,782 B1 | 3/2001 | Eliaz et al. |
| 6,232,344 B1 | 5/2001 | Feng et al. |
| 6,254,860 B1 | 7/2001 | Garst |
| 6,258,844 B1 | 7/2001 | Garst et al. |
| 6,262,105 B1 | 7/2001 | Johnstone |
| 6,350,442 B2 | 2/2002 | Garst |
| 6,403,649 B1 | 6/2002 | Woodward et al. |
| 6,441,047 B2 | 8/2002 | DeSantis et al. |
| 7,351,404 B2 | 4/2008 | Woodward et al. |
| 7,368,436 B2 | 5/2008 | Cleave |
| 7,388,029 B2 | 6/2008 | Delong et al. |
| 7,514,474 B1 | 4/2009 | Lipkin |
| 7,666,912 B2 | 2/2010 | Grosskreutz et al. |
| 8,038,988 B2 | 10/2011 | Woodward et al. |
| 8,101,161 B2 | 1/2012 | Woodward et al. |
| 8,263,054 B2 | 9/2012 | Woodward et al. |
| 8,758,733 B2 | 6/2014 | Ahluwalia et al. |
| 9,040,584 B2 | 5/2015 | Singer et al. |
| 9,089,579 B2 | 7/2015 | Kalayoglu |
| 9,138,480 B2 | 9/2015 | Trogden et al. |
| 9,149,484 B2 * | 10/2015 | Warner .............. A61K 31/5575 |
| 9,216,183 B2 | 12/2015 | Ahluwalia et al. |
| 2002/0044953 A1 | 4/2002 | Michelet et al. |
| 2002/0103255 A1 | 8/2002 | Hellberg et al. |
| 2002/0172693 A1 | 11/2002 | DeLong et al. |
| 2003/0083381 A1 | 5/2003 | Kumagai et al. |
| 2003/0147823 A1 | 8/2003 | Woodward et al. |
| 2003/0199590 A1 | 10/2003 | Cagle et al. |
| 2004/0052760 A1 | 3/2004 | Michelet et al. |
| 2005/0222232 A1 | 10/2005 | Delong et al. |
| 2007/0078175 A1 | 4/2007 | Boulle et al. |
| 2007/0160562 A1 | 7/2007 | Brinkenhoff |
| 2007/0269379 A1 * | 11/2007 | Mitragotri .......... G01N 33/5082 424/9.2 |
| 2007/0286890 A1 | 12/2007 | Walt et al. |
| 2008/0070988 A1 | 3/2008 | Woodward et al. |
| 2008/0207560 A1 | 8/2008 | Harada et al. |
| 2008/0275118 A1 | 11/2008 | Shaw et al. |
| 2009/0018204 A1 | 1/2009 | Brinkenhoff |
| 2009/0053290 A1 | 2/2009 | Sand et al. |
| 2009/0203659 A1 | 8/2009 | Woodward et al. |
| 2009/0270392 A1 | 10/2009 | Old et al. |
| 2010/0204335 A1 | 8/2010 | Beddingfield et al. |
| 2011/0002866 A1 | 1/2011 | Lubit et al. |
| 2011/0112198 A1 | 5/2011 | Gore et al. |
| 2012/0129789 A1 | 5/2012 | Yoelin |
| 2012/0251613 A1 | 10/2012 | Jain et al. |
| 2012/0322882 A1 | 12/2012 | Trogden et al. |
| 2013/0030055 A1 | 1/2013 | Walt et al. |
| 2013/0041025 A1 | 2/2013 | Walt et al. |
| 2013/0131097 A1 | 5/2013 | Ahluwalia et al. |
| 2014/0155488 A1 | 6/2014 | Warner et al. |
| 2014/0221493 A1 | 8/2014 | Ahluwalia et al. |
| 2014/0371320 A1 | 12/2014 | Trogden et al. |
| 2015/0328108 A1 | 11/2015 | Trogden et al. |
| 2016/0199277 A1 | 7/2016 | Trogden et al. |

FOREIGN PATENT DOCUMENTS

| | | |
|---|---|---|
| CA | 2174655 | 4/1995 |
| CA | 1339132 | 7/1997 |
| EP | 0170258 | 2/1986 |
| EP | 0249194 | 12/1987 |
| EP | 0308135 | 3/1989 |
| EP | 0321870 | 6/1989 |
| EP | 0639563 | 2/1995 |
| FR | 2239458 | 7/1973 |
| JP | S49-069636 | 7/1974 |
| JP | 61-218510 | 9/1986 |
| JP | H05-0331025 | 12/1993 |
| JP | H09-295921 | 11/1997 |
| JP | 10-287532 | 10/1998 |
| KR | 20080078795 | 8/2008 |
| WO | 89-03384 | 4/1989 |
| WO | 95-11003 | 4/1995 |
| WO | 97-31895 | 9/1997 |
| WO | 98-33497 | 8/1998 |
| WO | 99-12895 | 3/1999 |
| WO | 00-54810 | 9/2000 |
| WO | 01-74307 | 10/2001 |
| WO | 01-74313 | 10/2001 |
| WO | 01-74315 | 10/2001 |
| WO | 03066008 | 8/2003 |
| WO | 2007074602 | 7/2007 |
| WO | 2007-143568 | 12/2007 |
| WO | 2009-011744 | 1/2009 |
| WO | 2011-057129 | 5/2011 |
| WO | 2011057129 | 5/2011 |
| WO | 2011-119748 | 9/2011 |
| WO | 2012-068515 A2 | 5/2012 |
| WO | 2012-112451 | 8/2012 |

OTHER PUBLICATIONS

Abramovitz, Mark, Cloning and Expressing of a cDNA for the Human prostanoid FP Receptor, Journal of Biological Chemistry, 1994, 2632-2636, 269(4).

Adis Data Information, ZD 6416, 2003.

Adis, Alprostadil (NexMed) Alprox-TDTM, BefarTM, FemproxTM, Prostaglandin E1 (NewMed), Adis R & D Profile, 1999, 413-414, 2(6), Adis International Limited.

Al-Sereiti, M.R., Pharmacology of Rosemary (Rosmarinus Officinalis Linn.) and its Therapeutic Potentials, Indian Journal of Experimental Biology, 1999, 124-130, 37.

Allergan Clinical Study Report, 192024-008, 2000.

Allergan, Inc., Dermatologic and Ophthalmic Drugs Advisory Committee Briefing Document for Bimatoprost Solution 0.03%, Dermatologic and Ophthalmic Drugs Advisory Committee Briefing Document for Bimatoprost Solution 0.03%, Oct. 29, 2008, 1-108.

Allergan, Inc., Lumigan Package Insert, NDA 21-275, Mar. 2001, 6 Pages, NDA 21-275.

Alm, Albert et al, Effects on Intraocular Pressure and Side Effects of 0.005% Latanoprost Applied Once Daily, Evening or Morning, Ophthalmology, 1995, 1743-1752, 102.

(56) References Cited

OTHER PUBLICATIONS

Alm, Albert et al, Phase III Latanoprost Studies in Scandinavia, the United Kingdom and the United States, Survey of Ophthalmology, Feb. 1997, S105-S110, 41(2).
Alm, Albert et al, Uveoscleral Outflow—A Review, Experimental Eye Research, 2009, 760-768, 88(4).
Alm, Albert, The Potential of Prostaglandin Derivates in Glaucoma Therapy, Current Opinion in Ophthalmology, 1993, 44-50, 4(11).
Audoly, Laurent et al, Identification of Specific EP Receptors Responsible for the Hemodynamic Effects of PGE2, Am. J. Physiol., 1999, H924-H930, 277.
Badawy, Sherif et al, Salt Selection for Pharmaceutical Compounds, Preformulation in Solid Dosage Form Development (Informa Healthcare), 2008, 63-80, Chapter 2.3, Adeyeyem, Moji, ed.
Bartmann, W., Synthesis and Biological Activity, Luteolytic Prostaglandins, Feb. 1979, 301-311, 17(2).
Bastin, Richard et al, Salt Selection and Optimisation Procedures for Pharmaceutical New Chemical Entities, Organic Process Research & Development, 2000, 427-435, 4.
Bean, Gerald, Commercially Available Prostaglandin Analogs for the Reduction of Intraocular Pressure: Similarities and Differences, Survey of Ophthalmology, 2008, S69-S84, 53 (Supp. 1).
Beisecker, Analee et al, Side Effects of Adjuvant Chemotherapy: Perceptions of Node-Negative Breast Cancer Patients, Psycho-Oncology, 1997, 85-93, 6.
Berge, Stephen M., Pharmaceutical Salts, Journal of Pharmaceutical Sciences, Jan. 1977, 1-19, 66 (1), US.
Berglund, Barbara et al, Investigation of Structural Analogs of Prostaglandin Amides for Binding to and Activation of CB1 and CB2 Cannabinoid Receptors in Rat Brain and Human Tonsils, Adv Exp Med Biol, 1999, 527-533, 469.
Bito, L.Z. et al, Long-Term Maintenance of Reduced Intraocular Pressure by Daily or Twice Daily Topical Application of Prostaglandins to Cat or Rhesus Monkey Eyes, Investigative Ophthalmology & Visual Science, 1983, 312-319, 24(3).
Bito, Laszlo, A new approach to the medical management of glaucoma, from the bench to the clinic, and beyond, Investigative Ophthalmology & Visual Science, 2001, 1126-1133, 42(6), The Proctor Lecture.
Botchkarev, Vladimir, Molecular Mechanisms of Chemotherapy-Induced Hair Loss, JID Symposium Proceedings, 2003, 72-75, 8.
Brandt, James et al, Comparison of Once- or Twice-Daily Bimatoprost with Twice-Daily Timolol in Patients with Elevated IOP, American Academy of Ophthalmology, 2001, 1023-1031, 108(6).
Brandt, James, PA022 Phase III, 3-month Comparison in Timolol with AGN-192024: A New Ocular Hypotensive Lipid for Glaucoma Management, Presented at 2000 Am. Acad. Ophthalmology, Ann. Mtg., Oct. 23, 2000, 1 Page.
Brubaker, Richard et al, Effects of AGN 192024, a new Ocular Hypotensive Agent, on Aqueous Dynamics, American journal of Ophthalmology, 2001, 19-24, 131(1).
Brundy, Gordon, Synthesis of 17-Phenyl-18, 19, 20-Trinorprostaglandins I. The PG1 Series, Prostaglandins, 1975, 1-4, 9(1).
Business Wire, Phase III Lumigan, AGN-192024—Data Presented At American Academy of Ophthalmology, American Academy of Ophthalmology, 2000, 1-3, Retrieved Dec. 14, 2010.
Cadet, Patrick et al, Molecular Identification and Functional Expression of µ3, a Novel Alternatively Spliced Variant of the Human µ Opiate Receptor Gene, J. Immunol., 2003, 5118-5123, 170.
Camras, Carl B. et al, Bimatoprost, the Prodrug of a Prostaglandin Analogue, Br J Ophthalmol, 2008, 862-863, 92.
Camras, Carl B. et al, Comparison of Latanoprost and Timolol in Patients with Ocular Hypertension and Glaucoma, Ophthalmology, 1996, 138-147, 103(1).
Camras, Carl B. et al, Detection of the Free Acid of Bimatoprost in Aqueous Humor Samples From Human Eyes Treated with Bimatoprost Before Cataract Surgery, The American Academy of Ophthalmology, 2004, 2193-2198, 7pg.
Camras, Carl B. et al, Latanoprost, a prostaglandin Analog, for Glaucoma Therapy, Ophthalmology, 1996, 1916-1924, 103(11).
Camras, Carl B. et al, Multiple Dosing of Prostaglandin F2α or Epinephrine on Cynomolgus Monkey Eyes, Investigative Ophthalmology & Visual Science, Sep. 1988, 1428-1436, 29(9).
Camras, Carl B. et al, Multiple Dosing of Prostaglandin F2α or Epinephrine on Cynomolgus Monkey Eyes, Investigative Ophthalmology & Visual Science, 1987, 463-469, 28(3).
Camras, Carl B. et al, Multiple Dosing of Prostaglandin F2α or Epinephrine on Cynomolgus Monkey Eyes, Investigative Ophthalmology & Visual Science, 1987, 921-926, 28(6).
Camras, Carl B. et al, Reduction of Intraocular Pressure in Normal and Glaucomatous Primate (Aotus Trivirgatus) Eyes by Topically Applied Prostaglandin F2α, Current Eye Research, 1981, 205-209, 1 (4).
Cantor, Louis et al, Levels of Bimatoprost Acid in the Aqueous Humour After Bimatoprost Treatment of Patients with Cataract, Br. J. Ophthalmol, 2007, 629-632, 91.
Cantor, Louis et al, Reply-Bimatoprost, the Prodrug of a Prostaglandin Analogue, Br J Ophthalmol, 2008, 863-864, 92.
CAS RN 155206-00-1 May 20, 1994.
Cayatte, Antonio et al, The Thromboxane A2 Receptor Antagonist, S18886, Decreases atherosclerotic Lesions and serum Intracellular Adhesion Molecule-1 in the Apo E Knockout Mouse, 71st Scientific Sessions, 1998, I-115 (Abstract), 98(17).
Chen, June et al, AGN 191129: A Neutral Prostaglandin F2n (PGF2n) Analog That Lacks the Mitogenic and Uterotonic Effects Typical of FP Receptor Agonists, Glaucoma, Anatomy & Pathology, Physiology & Pharmacology, 1999, 3562-B420, 40(4).
Chen, June et al, Replacement of the Carboxylic Acid Group of Prostaglandin F2α (PGF2α) with Certain Non-Ionizable Substituents Results in Pharmacologically Unique Ocular Hypotensive Agents, 11th Intl Conf. Advances Prostaglandin & Leukotriene Res.: Basic Sci. & New Clinical Applications—Abstract Book, 2000, 1 page.
Chen, June et al, Studies on the Pharmacology of Prostamide F2α, A Naturally Occurring Substance, Brit. J. Pharmacology, 2001, 63P, 133.
Chyun, Yong et al, Stimulation of Bone Formation by Prostaglandin E2, Prostaglandins, 1984, 97-103, 27(1).
Clissold, D., The Potential for Prostaglandin Pharmaceuticals, Lipids in Health and Nutrition, 1999, 115-129, 244, The Royal Society of Chemistry.
Cohen, Joel, Enhancing the Growth of Natural Eyelashes: The Mechanism of Bimatoprost-Induced Eyelash Growth, Dermatol Surg, 2010, 1361-1371, 36(9).
Coleman, Robert et al, Prostanoids and Their Receptors, Comprehensive Medicinal Chemistry, 1990, 643-714, 3.
Coleman, Robert, VIII. International union of Pharmacology Classification of Prostanoid Receptors: Properties, Distribution, and Structure of the Receptors and Their Subtypes, The American Society for Pharmacology and Experimental Therapeutics, 1994, 205-229, 26(2).
Collins, Paul et al, Synthesis of Therapeutically Useful Prostaglandin and Prostacyclin Analogs, Chem. Rev., 1993, 1533-1564, 93.
Corsini, A. et al, (5Z)-Carbacyclin Discriminates Between Prostacyclin-Receptors Coupled to Adenylate Cyclase in Vascular Smooth Muscle and Platelets, Br. J. Pharmac., 1987, 255-261, 90.
Cowley, Lorraine et al, How Women Receiving Adjuvant Chemotherapy for Breast Cancer Cope With Their Treatment: a Risk Management Perspective, Journal of Advanced Nursing, 2000, 314-321, 31(2).
Cox, Colin et al, Protein Fabrication Automation, Protein Science, 2007, 379-390, 16.
Crowston, Jonathan et al, Effect of Bimatoprost on Intraocular Pressure in prostaglandin FP Receptor Knockout Mice, Investigative Ophthalmology & Visual Science, 2005, 4571-4577, 46.
Darnell, J., Cell-to-Cell Signaling: Hormones and Receptors, Molecular Cell Biology, 1990, 738-743, vol. 82, Darnell, J., Lidish, H., Baltimore, D., Eds., New York, New York.
Davies, Sean, Hydrolysis of Bimatoprost (Lumigan) to Its Free Acid by Ocular Tissue In Vitro, Journal of Ocular Pharmacology and Therapeutics, 2003, 45-54, 19(1).

(56) References Cited

OTHER PUBLICATIONS

De Asua, L Jimenez et al, The Stimulation of the Initiation of DNA Synthesis and Cell Division in Swiss Mouse 3T3 Cells by Prostaglandin F2α Requires Specific Functional Groups in the Molecule, J. Biol. Chemistry, 1983, 8774-8780, 256(14).

Dean, T.R. et al, Improvement of Optic Nerve Head Blood Flow After One-Week Topical Treatment with Travoprost (AL06221) in the Rabbit, Investigative Ophthalmology & Visual Science, Mar. 15, 1999, 2688-B563, 40(4).

Del Toro, F. et al, Characterization of Prostaglandin E2 Receptors and Their Role in 24,25-(OH)2D3-Mediated Effects on Resting Zone Chondrocytes, Journal of Cellular Physiology, 2000, 196-208, 182.

Delong, Mitchell, Prostaglandin Receptor Ligands: Recent Patent Activity, IDrugs, 2000, 1039-1052, 3(9).

Depperman, William, Up-To-Date Scalp Tonic, Book Reviews, 1970, 1115, 283(20).

Dirks, Monte et al, Efficacy and Safety of the Ocular Hypotensive Lipid™ 192024 in Patients with Elevated IOP: A 30-Day Comparison with Latanoprost, Investigative Ophthalmology & Visual Science, Mar. 15, 2000, S514, 41(4).

Dubiner, Harvey, Efficacy and Safety of Bimatoprost in Patients With Elevated Intraocular Pressure: a 30-Day Comparison With Latanoprost, Surv. Ophthalmol, 2001, S353-S560, 45 (4).

Easthope, Stephanie et al, Topical Bimatoprost, Drug Aging, 2002, 231-248, 19(3).

Eisenberg, Dan et al, A Preliminary Risk-Benefit Assessment of Latanoprost and Unoprostone in Open-Angle Glaucoma and Ocular Hypertension, Drug Safety, 1999, 505-514, 20(6).

Ellis, Cathy et al, Metabolism of Prostaglandin D2 in the Monkey*, The Journal of Biological Chemistry, 1979, 4152-4163, 254(10).

Enyedi, Laura et al, The Effectiveness of Latanoprost for the Treatment of Pediatric Glaucoma, J AAPOS, 1999, 33-39, 3(1).

Fagien, Steven, Management of Hypotrichosis of the Eyelashes: Focus on Bimatoprost, Clinical, Cosmetic and Investigational Dermatology, 2010, 39-48, 3.

Fagot, Dominique et al, Mitogenic Signaling by Prostaglandins in Chemically Transformed Mouse Fibroblasts: Comparison with Phorbol Esters and Insulin, Endocrinology, 1993, 1729-1734, 132(4).

Fall, P.M., Inhibition of Collagen Synthesis by Prostaglandins in the Immortalized Rat Osteoblastic Cell Line Pyla: Structure-Activity Relations and Signals Transduction Mechanisms, J. Bone Miner Res., 1994, 1935-1943, 9(12).

Faulkner, Robert, Aqueous Humor Concentrations of Bimatoprost Free Acid, Bimatoprost and Travoprost Free Acid in Cataract Surgical Patients administered Multiple Topical Ocular Doses of LUMIGAN or TRAVATAN, Journal of Ocular Pharmacology and Therapeutics, 2010, 147-156, 26(2).

FDA Approves Two New intraocular Pressure Lowering Drugs for the Management of Glaucoma, Mar. 16, 2001, FDA News.

FDA Label for Approved NDA 22-184 of Lumigan 0.01% and Lumigan 0.03%, Aug. 31, 2010.

Fiscella, Richard, Peek into the Drug Pipeline, Review of Optometry Online, Jan. 15, 2001, 5 pages.

Fitzpatrick, F.A., Separation of Prostaglandins and Thromboxanes by Gas Chromatography with Glass Capillary Columns, Analytical Chemistry, 1978, 47-52, 50(1).

Flisiak, Robert et al, Effect of Misoprostol on the Course of Viral Hepatitis B, Hepato-Gastroenterology, 1997, 1419-1425, 44.

Freedman, Tovia et al, Social and Cultural Dimensions of Hair Loss in Women Treated for Breast Cancer, Cancer Nursing, 1994, 334-341, 17(4).

Frenkel, R E et al, Evaluation of Circadian Control of Intraocular Pressure After a Single Drop of Bimatoprost 0.03% or Travoprost 0.004%, Curr. Med. Res. Opin., Apr. 2008, 919-923, 24(4).

Funk, Colin et al, Cloning and Expression of a cDNA for the Human Prostaglandin E Receptor EP1 Subtype*, The Journal of Biological Chemistry, Dec. 15, 1993, 26767-26772, 268(35).

Gandolfi, Stefano, Three-month Comparison of Bimatoprost and Latanoprost in Patients With Glaucoma and Ocular Hypertension, Adv. Ther., 2001, 110-121, 18.

Garadi, R et al, Travoprost: A New Once-Daily Dosed Prostaglandin for the Reduction of Elevated Intraocular Pressure, Investigative Ophthalmology & Visual Science, 1999, 4378-B181, Abstract.

Geng, Ling et al, Misoprostol, A PGE1 Analog That is Radioprotective for Murine Intestine and Hair, Induces Widely Different Cytokinetic Changes in These Tissues, The Journal of Investigative Dermatology, 1996, 858, 106(4).

Geng, Ling et al, Topical or Systemic 16,16 dm Prostaglandin E2 or WR-2721 (WR-1065) Protects Mice From Alopecia After Fractionated Irradiation, Int. J. Radiat. Biol., 1992, 533-537, 61(4).

Gerth, Jeff et al, Drug Makers Reap Profits on Tax-Backed Research, New York Times, Apr. 23, 2000, 10 pages.

Giuffre, Giuseppe, The Effects of Prostaglandin F2α in the Human Eye, Graefe's Archive Clin. & Exper. Ophthal., 1985, 139-141, 222.

Griffin, Brenda et al, AL-8810: A Novel Prostaglandin F2α Analog with Selective Antagonist Effects at the Prostaglandin F2α (FP) Receptor, Journal of Pharmacology and Experimental Therapeutics, 1999, 1278-1284, 290(3).

Grow (Verb) Definition, Merriam Webster's Dictionary, Retrieved from http://www.merriam-webster.com/dictionary/growing on Jul. 9, 2012.

Hall, Alistair et al, Clinprost Tijin, Current Opinion in Cardiovascular, Pulmonary & Renal Investigational Drugs, 1999, 605-610, 1(5).

Hallinan, Ann et al, Aminoacetyl Moiety as a Potential Surrogate for Diacylhydrazine Group of SC-51089, a Potent PGE2 Antagonist, and Its Analogs, J Med Chem, 1996, 609-613, 39.

Hanson, W R et al, 16,16 dm Prostaglandin2 Protects From Acute Radiation-Induced Alopecia in Mice, Clinical Research, 1988, 906A, 36(6).

Hanson, W R et al, Subcutaneous or Topical Administration of 16,16 Dimethyl Prostaglandin E2 Protects From Radiation-Induced Alopecia in Mice, Int. J. Radiation Oncology Biol. Phys., 1992, 333-337, 23.

Hartke, J.R. et al, Prostanoid FP Agonists Build Bone in the Ovariectomized Rat, Prostanoid FP Agonists Build Bone in the Ovariectomized Rat, 1999, S207.

Hayashi, Masaki et al, Prostaglandin Analogues Possessing Antinidatory Effects. 1. Modification of the ω Chain, J. Med. Chem., 1980, 519-524, 23.

Hecker, Markus et al, Studies on the Interaction of Minoxidil with Prostacyclin Synthase in Vitro, Biochemical Pharmacology, 1988, 3363-3365, 37(17).

Hellberg, Mark et al, The Hydrolysis of the Prostaglandin Analog Prodrug Bimatoprost to 17-Phenyltrinor PGF2α by Human and Rabbit Ocular Tissue, J. Ocular Pharmacol. Ther., 2003, 97-103, 19(2).

Higginbotham, Eve et al, One-Year, Randomized Study Comparing Bimatoprost and Timolol in Glaucoma and Ocular Hypertension, Archives of Ophthalmology, Oct. 2002, 1286-1293, 120 (10), US.

Houssay, Alerto, Effects of Prostaglandins Upon Hair Growth in Mice, Acta Physiol. Latinoam., 1976, 186-191, 26.

Huang, A. et al, Different Modes of Inhibition of Increase in Cytosolic Calcium and Aggregation of Rabbit Platelets by Two Thromboxane A2 Antagonists, Asia Pacific Journal of Pharmacology, 1994, 163-171, 9.

Hulan, H.W. et al, The Development of Dermal Lesions and Alopecia in Male Rats Fed Rapeseed Oil, Canadian Journal of Physiology and Pharmacology, 1976, 1-6, 54(1).

Hulan, H.W. et al, The Effect of Long-Chain Monoenes on Prostaglandin E2 Synthesis by Rat Skin, Lipids, 1977, 604-609, 12(7).

Hunt, Nigel et al, The Psychological Impact of Alopecia, BMJ, Oct. 2005, 951-953, 331.

Ichikawa, A. et al, Molecular Aspects of the Structures and Functions of the Prostaglandin E Receptors, J. Lipid Mediators Cell Signalling, 1996, 83-87, 14.

Informa UK Ltd., AGN-192024, 2006, 3 Pages.

Inoue, Hironishi, Thromboxane A2 receptor antagonists, Oct. 1996, 1221-1225, 32(10), Pharmaceutical Society of Japan.

(56) References Cited

OTHER PUBLICATIONS

International Search Report & Written Opinion mailed on Jul. 24, 2014 for PCT/US14/15430 filed on Feb. 7, 2014 in the name of Allergan, Inc.

J Am Pharm Assoc, Agents for Glaucoma, New Drugs of 2001, 2001, 4 pages, 42(2), Journal of the American Pharmaceutical Association, http://www.edscape.com/viewarticle/436631_22, US.

Jakobsson, Per-Johan et al, Membrane-Associated Proteins in Eicosanoid and Glutathione Metabolism (MAPEG), American Journal of Respiratory and Critical Care Medicine, 2000, S20-S24, 161.

Jimenez, J.J. et al, Stimulated Monocyte-Conditioned Media Protect From Cytosine Arabinoside-Induced Alopecia in Rat, Friday Afternoon Subspecialty Meetings, 1990, 973A.

Johnstone, M.A., Brief Latanoprost RX Induces Hypertrichosis, Glaucoma Clinical Pharmacology II Poster Presentation, 1998, S258, 39(4).

Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).

Jordan, B.A. et al, G-Protein-Coupled Receptor Heterodimerization Modulates Receptor Function, Nature, Jun. 17, 1999, 697-700, 399(6737).

Karim, S.M. et al, Prostaglandins and Human Respiratory Tract Smooth Muscle: Structure Activity Relationship, Advances in Prostaglandin and Thromboxane Research, 1980, 969-980, 7.

Katz, L.J. et al, Comparison of Human Ocular Distribution of Bimatoprost and Latanoprost, 2010, P450.

Kaufman, Paul, Effects of Intracamerally Infused Prostaglandins on Outflow Facility in Cynomolgus Monkey Eyes with Intact or Retrodisplaced Ciliary Muscle, Experimental Eye Research, 1986, 819-827, 43.

Kende, Andrew et al, Prostaglandin Phosphonic Acids Through Homolytic Halodecarboxylation of Prostaglandins F1α and F2α, Tetrahedron Letters, 1999, 8189-8192, 40.

Kerstetter, J.R. et al, Prostaglandin F2α-1-Isopropylester Lowers Intraocular Pressure Without Decreasing Aqueous Humor Flow, American Journal of Ophthalmology, 1988, 30-34, 105.

Kiriyama, Michitaka et al, Ligand Binding Specificities of the Eight Types and Subtypes of the Mouse Prostanoid Receptors Expressed in Chinese Hamster Ovary Cells, British Journal of Pharmacology, 1997, 217-224, 122.

Kluender, Harold et al, The Synthesis of Dimethylphosphonoprostaglandin Analogs, Prostaglandins and Medicine, 1979, 441-444, 2.

Krauss, Achim et al, Evidence for Human Thromboxane Receptor Heterogeneity Using a Novel Series of 9,11-Cyclic Carbonate Derivatives of Prostaglandin F2α, British Journal of Pharmacology, 1996, 1171-1180, 117.

Kvedar, Joseph et al, Topical Minoxidil in the Treatment of Male Pattern Alopecia, Pharmacotherapy, 1987, 191-197, 7(6).

Lachgar, S. et al, Effect of VEGF and Minoxidil on the Production of Arachidonic Acid Metabolites by Cultured Hair, Dermal Papilla Cells, Eur. J. Dermatol., 1996, 365-368, 6.

Lachgar, S. et al, Hair Dermal Papilla Cell Metabolism is Influenced by Minoxidil, Fundamental & Clinical Pharmacology, 1997, 178, 11(2).

Lachgar, S. et al, Modulation by Minoxidil and VEGF of the Production of Inflammatory Mediators by Hair Follicle Dermal Papilla Cells, Groupe de Rocherche Dermatologique, 1995, 161, 104(1).

Lambert, Joseph, Clinical Study Report, A Multicenter, Double-Masked, Randomized, Parallel, 3-Month study (with Treatment Extended to 1 year) of the Sa . . . , Study No. 192024-009, Phase 3, 1998, 34 pages, Allergan, Inc, US.

Lardy, C. et al, Antiaggregant and Antivasospastic Properties of the New Thromboxane A2 Receptor Antagonist Sodium 4-[[1-[[[(4 Chlorophenyl)sulfony]amino]methyl]cyclopentyl]methyl]benzeneacetate, Arzneim.-Forsch./Drug Res., 1994, 1196-1202, 44(11).

Law, Simon, Bimatoprost in the Treatment of Eyelash Hypotrichosis, Clinical Ophthalmology, 2010, 349-358, 4.

Lee, Ping-Yu et al, The Effect of Prostaglandin F2α on Intraocular Pressure in Normotensive Human Subjects, Investigative Ophthalmology & Visual Science, Oct. 1988, 1474-1477, 29(10).

Lee, Vincent et al, Improved Ocular Drug Delivery with Prodrugs, Prodrugs: Topical and Ocular Drug Delivery, 1992, 221-297, Kenneth Sloan Edition.

Lemieux, Julie et al, Chemotherapy-Induced Alopecia and Effects on Quality of Life Among Women With Breast Cancer: a Literature Review, Psycho-Oncology, 2008, 317-328, 17.

Liang, Y. et al, Identification and Pharmacological Characterization of the Prostaglandin FP Receptor and FP Receptor Variant Complexes, Br. J. Pharmacol., 2008, 1079-1093, 154.

Liljebris, Charlotta et al, Derivatives of 17-Phenyl-18,19,20-trinorprostaglandin F2α Isopropyl Ester: Potential Antiglaucoma Agents, J. Med. Chem., 1995, 289-304, 38.

Ling, Geng et al, 16,16 dm Prostaglandin E2 Protects Mice From Fractionated Radiation-Induced Alopecia, Clinical Research, 1990, 858A, 38(3).

Lumigan 6-Month Phase 3 Data Presented at American Glaucoma Society Meeting, Mar. 2, 2001, 4 pages, Business Wire.

Lundy, M.W. et al, Restoration of Cancellous Architecture and Increased Bone Strength in Aged Osteopenic Rats Treated with Fluprostenol, 21st Annual Meeting of the American Society for Bone and Mineral Research, 1999, S401.

Luoma, Minna-Liisa et al, The Meaning of Quality of Life in Patients Being Treated for Advanced Breast Cancer: a Qualitative Study, Psycho-Oncology, 2004, 729-739, 13.

Maddox, Yvonne et al, Amide and I-amino Derivatives of F Prostaglandins as Prostaglandin Antagonists, Nature, Jun. 15, 1978, 549-552, 273.

Malkinson, Frederick et al, Prostaglandins Protect Against Murine Hair Injury Produced by Ionizing Radiation of Doxorubicin, J. Invest. Dermatol., 1993, 135S-137S, 101.

Mansberger, Steven et al, Eyelash Formation Secondary to Latanoprost Treatment in a Patient With Alopecia, Arch. Ophthalmol., 2000, 718-719, 118.

Maruyama, Takayuki et al, EP1 Receptor Antagonists Suppress Tactile Allodynia in Rats, Prostaglandins & Other Lipid Mediators, 1999, 217(Abstract), 59.

Matsumura, H. et al, Brain and Neuroscience, 1998, 79-89.

Maw, Graham, Chapter 8. Pharmacological Therapy for the Treatment of Erectile Dysfunction, Annual Reports in Medicinal Chemistry, 1999, 71-80.

Maxey, Kirk, The Hydrolysis of Bimatoprost in Corneal Tissue Generates a Potent Prostanoid FP Receptor Agonist, Survey of Ophthalmology, Aug. 2002, S34-S40, 47 (Supp. 1).

McCullough, Peter et al, Ridogrel Janssen, Current Opinion in Anti-inflammatory & Immunodulatory Investigational Drugs, 1999, 265-276, 1(3).

McMurry, John, Amides, Organic Chemistry, 1984, 794.

Medical Review, Application No. 21-275, Center for Drug Evaluation and Research, 2001.

Medline, Bimatoprost (Ophthalmic), Bimatoprost, Jul. 24, 2001, 4 pages, Medlineplus. Health Information, Online.

Michelet, Jean-Francois et al, Activation of Cytoprotective Prostaglandin Synthase-1 by Minoxidil as a Possible Explanation for Its Hair Growth-Stimulating Effect, J. Invest. Dermatol., 1997, 205-209, 108.

Mihele, Densia et al, Cercetarea Actiunii Hepatoprotectoare A Unor Prostaglandine De Sinteza, Farmacia, 1999, 43-58, 67(5).

Millikan, Larry, Treatment of Alopecia, The Journal of Clinical Pharmacology, 1987, 715, 27(8).

Millikan, Larry, Treatment of Male Pattern Baldness, Drug Therapy, 1989, 62-73.

Mishima, Hiromu, A Comparison of Latanoprost and Timolol in Primary Open-Angle Glaucoma and Ocular Hypertension, Arch. Ophthalmol., 1996, 929-932, 114.

Miyamoto, Terumasa et al, A Comparison in the Efficacy and Safety Between Ramatroban (BAY u 3405) and Ozagrel-HCI for Bronchial Asthma—A Phase III, Multi-Center, Randomized, Double-Blind, Group Comparative Study, 1997, 599-639.

(56) References Cited

OTHER PUBLICATIONS

Mori, S. et al, Effects of Prostaglandin E2 on Production of New Cancellous Bone in the Axial Skeleton of Ovariectomized Rats, Bone, 1990, 103-113, 11.
Morris, Carrie et al, The Role of Bimatoprost Eyelash Gel in Chemotherapy-Induced Madarosis: An Analysis of Efficacy and Safety, Int. J. Trichology, 2011, 84-91, 3(2).
Moses, Robert, Adler's Physiology of the Eye, 1970, 1-18, 5th Ed.
Murakami, T. et al, Effect of Isocarbacyclin Methyl Ester Incorporated in Lipid Microspheres on Experimental Models of Peripheral Obstructive Disease, Drug Res., 1995, 991-994, 45(9).
Narumiya, Shuh et al, Roles of Prostanoids in Health and Disease; Lessons From Receptor-Knockout Mice, Common Disease: Genetic and Pathogenetic Aspects of Multifactorial Diseases, 1999, 261-269.
Neau, Steven, Pharmaceutical Salts, Water-Insoluble Drug Formulation, 2008, 417-435.
Negishi, Manabu et al, Molecular Mechanisms of Diverse Actions of Prostanoid Receptors, Biochimica et Biophysica Acta, 1995, 109-120, 1259.
New Drugs for Glaucoma, FDA Consumer Magazine, May-Jun. 2001.
Nora Hick, International Search Report & Written Opinion, ISA, Jun. 12, 2012, 14 pages, N/A.
Norrdin, R.W. et al, The Role of Prostaglandins in Bone in Vivo, Prostaglandins Leukotrienes and Essential Fatty Acids, 1990, 139-149, 41.
Ochoa, Blanca, Instilled Bimatoprost Ophthalmic Solution in Patients with Eyelash Alopecia Areata, Letters, Sep. 1, 2009, 530-532, 61(3), J. Am. Acad. Dermatol.
Olsen, Elise et al, Transdermal Viprostol in the Treatment of Male Pattern Baldness, J. Am. Acad. Dermatol., 1990, 470-472, 23.
Orlicky, D.J., Negative Regulatory Activity of a Prostaglandin F2α Receptor Associated Protein (FPRP), Prostaglandins, Leukotrienes and Essential Fatty Acids, 1996, 247-259, 54(4).
Ortonne, Jean-Paul et al, Hair Melanin's Hair Color: Ultrastructural and Biochemical Aspects, Journal of the Society for Investigative Dermatology, 1993, 82S-89S.
Paragraph IV Letter, Jul. 26, 2010.
Pfeiffer, N, New Developments in Glaucoma Drug Therapy, Ophthalmologist, 1992, W1-W13, 89.
Pharmaprojects No. 6321, 2006, 1 page.
Phase 3 Lumigan—AGN 192024—Data Presented At American Academy of Ophthalmology, Allergan Press Release, Mar. 1, 2000.
Physicians' Desk Reference, 56th ed., pp. 212-213, 543, 553-554, 2864-2865 (2002).
Poyer, J. F. et al, Prostaglandin F2α Effects on Isolated Rhesus Monkey Ciliary Muscle, Invest. Ophthalmol. Vis. Sci., Nov. 1995, 2461-2465, 36(12).
Preparation of '404 Patent Documents for European Patent Office; Defendant Athena Cosmetics, Inc., Supplemental Invalidity Contentions Pursuant to Patent Local Rule 3-3, 2009.
Preparation of '404 Patent Documents for European Patent Office; Defendant Peter Thomas Roth Labs LLC and Peter Thomas Roth, Inc.'s Invalidity Contentions Pursuant to Patent Local Rule 3-3, 2009.
Preparation of '404 Patent Documents for European Patent Office; Defendants Metrics LLC, Product Innovations LLC; Stella International LLC; and Nutra-Luxe, M.D. LLC's; Local Patent Rule 3-3 Preliminary Invalidity Contentions, 2009.
Preparation of '404 Patent Documents for European Patent Office; Invalidity Contentions Pursuant to Patent Local Rule 3-3, 2008.
Pucci, Neri et al, Long Eyelashes in a Case Series of 93 Children With Vernal Keratoconjunctivitis, Pediatrics, 2005, e86-e91, 115.
Rampton, D.S. et al, Anti-inflammatory Profile in Vitro of Ridogrel, A Putative New Treatment for Inflammatory Bowel Disease, Immunology, Microbiology, and Inflammatory Disorders, 1999, G3477.
Resul, B et al, Phenyl-substituted Prostaglandins: Potent and Selective Antiglaucoma Agents, J. Med. Chem., Jan. 22, 1993, 243-248, 36(2).
Reynolds, A, Darkening of Eyelashes in a Patient Treated With Latanoprost, Eye, 1998, 741-743, 12.
Richer, Marie-Claire et al, Living in It, Living With It, and Moving On: Dimensions of Meaning During Chemotherapy, 2002, 113-119, 29(1).
Rigaudy, J. et al, Nomenclature of Organic Chemistry Sections A, B. C, D, E, F, and H, InCL Union of Pure & Applied Chemistry, Organic Chemistry Div., Comm'n on Nomenclature of Organic Chemistry, 1979, 255-256.
Roenigk, Henry, New Topical Agents for Hair Growth, Clinics in Dermatology, 1988, 119-121, 6(4).
Romano, Maria Rosaria et al, Evidence for the Involvement of Cannabinoid DB1 Receptors in the Bimatoprost-Induced Contractions on the Human Isolated Ciliary Muscle, Investigative Ophthalmology & Visual Science, Aug. 2007, 3677-3382, 48(8).
Roof, S.L. et al, mRNA Expression of Prostaglandin Receptors EP1, EP2, EP3 and EP4 in Human Osteoblast-Like Cells and 23 Human Tissues, 18 Annual Meeting of the American Society for Bone and Mineral Research, 1996, S337.
Roseborough, Ingrid et al, Lack of Efficacy of Topical Latanoprost and Bimatoprost Ophthalmic Solutions in Promoting Eyelash Growth in Patients with Alopecia Areata, J Am Acad Dermtol, Apr. 2009, 705-706, 60(4).
Ruel, Rejean et al, New Class of Biphenylene Dibenzazocinones as Potent Ligands for the Human EP1 Prostanoid Receptor, Bioorganic & Medicinal Chemistry Letters, 1999, 2699-2704, 9.
Sakuma, Yoko et al, Crucial Involvement of the EP4 Subtype of Prostaglandin E Receptor in Osteoclast Formation by Proinflammatory Cytokines and Lipopolysaccharide, Journal of Bone and Mineral Research, 2000, 218-227, 15(2).
Sauk, John et al, Influence of Prostaglandins E1, E2, and Arachidonate on Melanosomes in Melanocytes and Keratinocytes of Anagen Hair Bulbs in Vitro, The Journal of Investigative Dermatology, 1975, 332-337, 64.
Shaikh, M.Y. et al, Hypertrichosis of the Eyelashes From Prostaglandin Analog Use: a Blessing or a Bother to the Patient?, Journal of Ocular Pharmacology and Therapeutics, 2006, 76-77, 22(1).
Sharif, N.A. et al, [3H]AL-5848 ([3H]9β-(+)-Fluprostenol). Carboxylic Acid of Travoprost (AL-6221), a Novel FP Prostaglandin o Study the Pharmacology and Autoradiographic Localization of the FP Receptor, J. Pharm. Pharmacol., 1999, 685-694, 51.
Sharif, N.A. et al, Cat Iris Sphincter Smooth-Muscle Contraction: Comparison of FP-Class Prostaglandin Analog Agonist Activities, J. Ocul. Pharmacol. Ther., Apr. 2008, 152-163, 24(2).
Sharif, N.A. et al, Human Ciliary Muscle Cell Responses to FP-class Prostaglandin Analogs: Phosphoinositide Hydrolysis, Intracellular Ca2+ Mobilization and MAP Kinase Activation, J. Ocul. Pharmacol Ther., 2003, 437-455, 19.
Sharif, N.A. et al, Human Trabecular Meshwork cell Responses Induced by Bimatoprost, Travoprost, Unoprostone, and Other FP Prostaglandin Receptor Agonist Analogues, Invest. Ophthalmol Vis. Sci., 2003, 715-721, 44.
Sharif, N.A. et al, Ocular Hypotensive FP Prostaglandin (PG) Analogs: PG Receptor Subtype Binding Affinities and Selectivities, and Agonist Potencies at FP and Other PG Receptors in Cultured Cells, Journal of Ocular Pharmacology and Therapeutics, 2003, 501-515, 19(6).
Sharif, N.A. et al, Update and Commentary on the Pro-Drug Bimatoprost and a Putative Prostamide Receptor, Expert Rev. Ophthalmol., 2009, 477-489, 4(5).
Sharif, Najam, Bimatoprost and Its Free Acid Are Prostaglandin FP Receptor Agonists, European Journal of Pharmacology, 2001, 211-213, 432.
Sherwood, Mark et al, Six-Month Comparison of Bimatoprost Once-Daily and Twice-Daily with Timolol Twice-Daily in Patients with Elevated Intraocular Pressure, Survey of Ophthalmology, 2001, S361-S368, 45(4).
Shin, Mei-Shu et al, PGE2 Induces Regional Remodeling Changes in Haversian Envelope: a Histomorphometric Study of Fractured Ribs in Beagles, Bone and Mineral, 1986, 227-264, 1.
Shimazaki, Atsushi et al, Effects of the New Ethacrynic Acid Derivative SA9000 on Intraocular Pressure in Cats and Monkeys, Biol. Pharm. Bull., 2004, 1019-1024, 27(7).

(56) References Cited

OTHER PUBLICATIONS

Shimazaki, Atsushi et al, New Ethacrynic Acid Derivatives as Potent Cytoskeletal Modulators in Trabecular Meshwork Cells, Bio. Pharm. Bull., 2004, 846-850, 27(6).
Sjoquist, Birgitta et al, Ocular and Systemic Pharmacokinetics of Latanoprost in Humans, Surv. Ophthalmol., Aug. 2002, S6-S12, 47(Suppl 1).
Sjoquist, Birgitta et al, Pharmacokinetics of Latanoprost in the Cynomolgus Monkey. 3rd Communication: Tissue Distribution After Topical Administration on the Eye Studied by Whole Body Autoradiography, Glaucoma Research Laboratories. Arzneim-Forsch/Drug Res., 1999, 240-249, 49.
Sorbera, L.A. et al, Travoprost, Drugs of the Future, 2000, 41-45, 25(1).
Souillac, Pierre et al, Characterization of Delivery Systems, Differential Scanning Calorimetry, 1999, 212-227, 49.
Spada, C. S. et al, Bimatoprost and Prostaglandin F2α Selectively Stimulate Intracellular Calcium Signaling in Different Cat iris Sphincter Cells, Exp. Eye Res., Jan. 2005, 135-145, 80(1).
Sredni, Benjamin et al, The Protective Role of the Immunomodulator AS101 Against Chemotherapy-Induced Alopecia Studies on Human and Animal Models, Int. J. Cancer, 1996, 97-103, 65.
Stahl, Heinrich et al, Chapter 12: Monographs on Acids and Bases, Handbook of Pharmaceutical Salts, 2008, 265-327.
Stamer, W.D. et al, Cellular Basis for Bimatoprost Effects on Human Conventional Outflow, Invest. Ophthalmol. Vis. Sci., Oct. 2010, 5176-5181, 51(10).
Stjernschantz, Johan et al, From PGF2α-isopropyl Ester to Latanoprost: A Review of the Development of Xalatan: The Proctor Lecture, Invest Ophthalmol. Vis. Sci., May 2001, 1134-1145, 42(6).
Stjernschantz, Johan et al, Phenyl Substituted Prostaglandin Analogs for Glaucoma Treatment, Phenyl Substituted Prostaglandin Analogs for Glaucoma Treatment, 1992, 691-704, 17(8).
Stjernschantz, Johan et al, Studies on Ocular Inflammation and Development of a Prostaglandin Analogue for Glaucoma Treatment, Exp. Eye Res., Apr. 2004, 759-766, 78(4).
Supplement A (Lumigan®), Physician's Desk Reference 2001, Mar. 2001, A1-A2, 55.
Swarbrick, James et al, Salt Forms of Drugs and Absorption, Encyclopedia of Pharmaceutical Technology, 1988, 453-499, 13.
Terada, Nobuhisa et al, Effect of a Thromboxane A2 Receptor Antagonist Ramatroban (Bay u 3405), on Inflammatory Cells, Chemical Mediators and Non-Specific Nasal Hyperreactivity After Allergen Challenge in Patients with Perennial Allergic Rhinitis, Allergoloy International, 1998, 59-67, 47.
The Newsletter of Glaucoma Foundation, 2000, 11 pages, 11(2).
Tomita, Yasushi et al, Melanocyte-Stimulating Properties of Arachidonic Acid Metabolites: Possible Role in Postinflammatory Pigmentation, Pigment Cell Research, 1992, 357-361, 5.
Tosti, Antonella et al, Drug-Induced Hair Loss and Hair Growth: Incidence, Management and Avoidance, Drug Safety, 1994, 310-317, 10(4).
Tosti, Antonella et al, Hypertrichosis of the Eyelashes Caused by Bimatoprost, J Am Acad Dermatol, Nov. 2004, S149-S150, 51(5).
Travatan (travoprost ophthalmic solution) 0.004% Product Insert, NDA 21-257, Mar. 16, 2001, 7 Pages.
Trueb, Ralph, Chemotherapy-Induced Alopecia, Semin Cutan Med Surg, 2009, 11-14, 28.
U.S. Appl. No. 11/805,122, Resp. to Office Action dated Jan. 21, 2009.
Ueda, Ken et al, Cortical Hyperostosis Following Long-Term Administration of Prostaglandin E1 in Infants with Cyanotic Congenital Heart Disease, Journal of Pediatrics, 1980, 834-836, 97(5).
Ulrich, Jens et al, Skin Toxicity of Anti-Cancer Therapy, J Dtsch Dermatol Ges., 2008, 959-975, 6.
Van Alphen, G.W.H.M. et al, The effect of Prostaglandins on the Isolated Internal Muscles of the Mammalian Eye, Including Man, Documenta Ophthalmologica, 1977, 397-415, 42(4).
Vandenburg, A.M. et al, A One-Month Dose Response Study of AGN 192024, a Novel Antiglaucoma Agent, in Patients with Elevated Intraocular Pressure, Glaucoma Clinical Pharmacology IV Poster Presentation, 1999, S830, 40 (4).
Vandenburgh, Amanda, reply to Alan L. Robin, An Accurate Comparison of Bimatoprost's Efficacy and Adverse Effects, Arch Ophthalmol, Jul. 2002, 997-1000, 120.
Vayssairat, Michael, Preventive Effect of an Oral prostacyclin Analog, Beraprost Sodium, on Digital Necrosis in Systemic Sclerosis, J. Rheumatol, 1999, 2173-2178, 26.
Vengerovsky, A.I. et al, Hepatoprotective action of prostaglandins, Experimental and Clinical Pharmacology, 1997, 78-82, 60(5).
Verbeuren, T. et al, The TP-Receptor Antagonist S 18886 Unmasks Vascular Relaxation and Potentiates the Anti-Platelet Action of PGD2, New Antithrombotic Agents, Jun. 11, 1997, 693.
Vielhauer, G.A. et al, Cloning and Localization of hFP(S): a Six-Transmembrane mRNA Splice Variant of the Human FP Prostanoid Receptor, Arch Biochem Biophys., Jan. 15, 2004, 175-185, 421(2).
Villumsen, J. et al, Prostaglandin F2α-isopropylester Eye Drops: Effect on Intraocular Pressure in Open-Angle Glaucoma, Br. J. Ophthalmol., 1989, 975-979, 73.
Vincent, J.E. et al, Letter to the Editor Prostaglandin Synthesis and Selenium Deficiency a Hypothesis, Prostaglandins, 1974, 339-340, 8(4).
Vippagunta, Sudha et al, Crystalline Solids, Advanced Drug Delivery Reviews, 2001, 3-26, 48.
Voss, N.G. et al, Induction of Anagen Hair Growth in Telogen Mouse Skin by Topical Latanoprost Application, Glaucoma Pharmacology, Cellular, Mechanism II, Mar. 15, 1999, S676, 40(4).
Waddell, K.A. et al, Combined Capillary Column Gas Chromatography Negative Ion Chemical Ionization Mass Spectrometry of Prostanoids, Biomedical Mass Spectrometry, 1983, 83-88, 10(2).
Wand, Martin, Latanoprost and Hyperpigmentation of Eyelashes, Arch Ophthalmology, Sep. 1997, 1206-1208, 115.
Wang, Yili et al, Design and Synthesis of 13,14-Dihydro Prostaglandin F1α Analogues as Potent and Selective Ligands for the Human FP Receptor, J. Med. Chem., 2000, 945-952, 43.
Watson, Peter et al, A Six-month, Randomized, Double-masked Study Comparing Latanoprost with Timolol in Open-Angle Glaucoma and Ocular Hypertension, Ophthalmology, 1996, 126-137, 103.
Whitcup, Clinical Study Report, A Multi-Center, Investigator-Marked, Randomized, Parallel Study of the Safety and Efficacy of AGN 192024 0.03% Ophthalmic Solution Com . . . , Study No. 192024-010-01, Phase 3b, 1999, 1, Allergan.
White, J.H. et al, Heterodimerization is Required for the Formation of a Functional GABA(B) Receptor, Nature, Dec. 17, 1998, 679-682, 396(6712).
Whitson, Jess, Travoprost—a New Prostaglandin Analogue for the Treatment of Glaucoma, Expert Opin. Pharmacother, 2002, 965-977, 3 (7).
Williams, Adrian et al, Penetration Enhancers, Advanced Drug Delivery Reviews, 2004, 603-618, 56.
Williams, Jane et al, A Narrative Study of Chemotherapy-Induced Alopecia, 1999, 1463-1468, 26(9).
Willis, Anthony, Prostaglandins and Related Lipids, vol. I, Chemical and Biochemical Aspects, CRC Handbook of Eicosanoids, 1987, 80-97, 1.
Wilson, S.J. et al, Dimerization of the Human Receptors for Prostacyclin and Thromboxane Facilitates Thromboxane Receptor-Mediated CAMP Generation, J. Biol. Chem., Dec. 17, 2004, 53036-53047, 279(51).
Woodward, David et al, Bimatoprost Effects on Aqueous Humor Dynamics in Monkeys, J. Ophthalmol., 2010, 1-5, vol. 2010.
Woodward, David et al, Bimatoprost: a Novel Antiglaucoma Agent, Cardiovascular Drug Reviews, 2004, 103-120, 22(2).
Woodward, David et al, Emerging Evidence for Additional Prostanoid Receptor Subtypes, Current Topics in Pharmacology, 1998, 153-162, 4.
Woodward, David et al, Identification of an antagonist that selectively blocks the activity of prostamides (prostaglandin-ethanolamides) in the feline iris, British Journal of Pharmacology, 2007, 342-352, 150.

(56) References Cited

OTHER PUBLICATIONS

Woodward, David et al, Molecular Characterization and Ocular Hypotensive Properties of the Prostanoid EP2 Receptor, Journal of Ocular Pharmacology, 1995, 447-454, 11(3).

Woodward, David et al, Prostaglandin F2α (PGF2α) 1-Ethanolamide: A Unique Local Hormone Biosynthesized From Anandamide, 11th Intl Conf. Advances Prostaglandin & Leukotriene Res.: Basic Sci. & New Clinical Applications—Abstract Book 27, 2000, 1 page.

Woodward, David et al, Replacement of Carboxylic Acid Group of Prostaglandin F2α with a Hydroxyl or Methoxy Substituent Provides Biologically Unique Compounds, British Journal of Pharmacology, Aug. 2000, 1933-1943, 130(8).

Woodward, David et al, Studies on the Ocular Effects of Pharmalogically Novel Agent Prostaglandin F2α 1-OCH3 (AGN 191129), Eicosanoids, 1998, R719.

Woodward, David et al, The Pharmacology of Bimatoprost (LumiganTM), Surv Ophthalmol, 2001, S337-S345, Suppl 4.

Woodward, David, Pharmacological Characterization of a Novel Antiglaucoma Agent, Bimatoprost (AGN 192024), J. Pharmacol. Exp. Ther., Jan. 24, 2003, 772-785, 305 (2).

Xalatan (Latanoprost Ophthalmic Solution) 0.005% Product Insert, 2001, 4 Pages.

Xalatan® Eye Drops, Retrieval Date : Oct. 2, 2010, 3 pages, http://home.intekom.com/pharm/pharmaca/xalatan.html.

Yamaji, K. et al, Prostaglandins E1 and E2, but not F2α or Latanoprost, Inhibit Monkey Ciliary Muscle Contraction, Curr. Eye Res., Aug. 2005, 661-665, 30(8).

Yoelin, Steve et al, Safety, Effectiveness, and Subjective Experience with Topical Bimatoprost 0.03% for Eyelash Growth, Dermatol. Surg., 2010, 638-649, 36.

Zeigler, Tania, Old Drug New Use: New Research Shows Common Cholesterol-Lowering Drug Reduces Multiple Sclerosis Symptoms in Mice, National Institute of Neurological Disorders and Stroke, Jan. 6, 2003, 2 Pages.

Zimbric, M.L. et al, Effects of Latanoprost of Hair Growth in the Bald Scalp of Stumptailed Macaques, Glaucoma Pharmacology, Cellular Mechanism II, 1999, 3569-B427—Abstract, vol. 40, No. 4.

Bird, Katie, Nano Carriers Enhance Skin Penetration and Antioxidant Effect of CoQ10, Comestic design-asia.com, Apr. 8, 2010, 1 page, n/a, William Reed Business Media SAS.

Bundy, Gordon, Synthesis of 17-Phenyl-18, 19, 20-Trinorprostaglandins I. The PG1 Series, Prostaglandins 1975, 9:1-4 (1).

Emu Oil Hairloss and Frontal Regrowth, 2010, 4 pages, www.hairloss-research.org.blog/?p=73.

Krielgaard, Mads, Influence of Microemulsions on Cutaneous Drug Delivery, Advanced Drug Delivery Reviews, 2002, S77-S98, 54 Suppl. 1.

Muller-Rover, Sven et al., A Comprehensive Guide for the Accurate Classification of Murine Hair Foliciles in Distinct Hair Cycle Stages, J. Invest. Dermatol. 2001, 117: 3-15.

Mura, Simona et al., Penetration Enhancer-Containing Vesciles (PEV) as Carriers for Cutaneous Delivery of Minoxidil, Int'l. J. Pharmaceutics 2009, 380: 72-79.

Schneider, Marlon et al., The Hair Follicle as a Dynamic Miniorgan, Current Biology 2009, 19: R132-142.

Tobin, Desmond, Aging of the Hair Follicle Pigmentation System, Int'l. J. Trichology, Jul.-Dec. 2009, 1: 83-93 (2).

Topical Emu Oil and Coconut Oil for Hair Loss—A Potent Combination, 2010, 3 pages, www.hairloss-research.org/?p=15.

Uno, Hideo et al., Effect of Latanoprost on Hair Growth in the Bald Scalp of the Stump-Talied Macacque: A Pilot Study, Acta Derm Venereol. 2002, 82: 7-12.

Sigeru, Sekine et al, Handbook of Cosmetics, Oct. 30, 2006, 714, Nikko Chemicals Co. Ltd., Japan.

Block, Lawrence H., Medicated Applications in Remington's Pharmaceutical Sciences; Gennaro, A. Ed. 17th Edition, Mack Publishing Company, Easton, PA 1985, Ch. 88: 1567-1578.

Jover, Eric et al., Comparative characterization of a wool-wax extract by two complementary chromatographic techniques, J. Cosmet. Sci. 2006, 57: 23-35.

Trommer, H. et al., Overcoming the Stratum Corneum: The Modulation of Skin Penetration, Skin Pharmacol. Physiol. 2006, 19: 106-121.

Wolfmeier, Uwe et al., In Ullmann's encyclopedia of Industrial Chemistry, 39, published online Jun. 15, 2000, pp. 111-175, http://onlinelibrary.wiley.com/doi/10.1002/14356007.a28_103/pdf, retrieved Mar. 15, 2015.

\* cited by examiner

COMPOSITIONS AND METHODS FOR STIMULATING HAIR GROWTH

RELATED APPLICATION

This application is a continuation of U.S. patent application Ser. No. 14/163,954 filed Jan. 24, 2014, which is a continuation of U.S. patent application Ser. No. 12/940,711, which claims the benefit of U.S. Provisional Patent Application No. 61/259,368, filed Nov. 9, 2009, each of which are hereby incorporated by reference in their entireties.

FIELD OF THE INVENTION

Disclosed herein are compositions and methods for stimulating the growth of hair and treating disorders resulting in hair loss wherein said compositions include a cyclopentane heptanoic acid, 2-cycloalkyl or arylalkyl compound represented by the formula I:

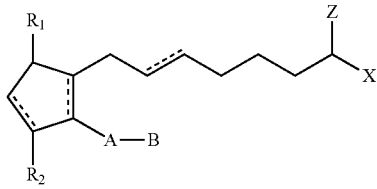

wherein the dashed bonds represent the presence or absence of a double bond which can be in the cis or trans configuration and A, B, Z, X, $R_1$ and $R_2$ are as defined in the specification and a penetration enhancer. Such compositions are used in stimulating hair growth of human or non-human animals.

BACKGROUND OF THE INVENTION

Dermatologists recognize many different types of hair loss, the most common being "alopecia" or "baldness" wherein humans (mostly males) begin losing scalp hair at the temples and on the crown of their head. However, hair loss may be due to many other disorders.

Hair loss is often accompanied by a change in the hair growth cycle. All mammalian hair passes through a life cycle that includes the anagen phase, the catagen phase and the telogen phase. The anagen phase is the period of active hair growth. In the scalp, this phase lasts from 3-5 years. The catagen phase is a short 1-2 week transitional phase between the anagen phase and the telogen phase. The final telogen phase is considered a "resting phase" where all growth ceases. This phase is also relatively short-lived lasting about 3-4 months before the hair is shed and a new one begins to grow. With the onset of baldness, a successively greater proportion of hairs are in the telogen phase with correspondingly fewer in the active growth anagen phase.

Additionally, different types of hair exist including terminal hairs, vellus hairs and modified terminal hairs. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. Modified terminal hairs are seen in eye lashes and eye brows. As alopecia progresses, a transition takes place wherein the hairs themselves change from the terminal to the vellus type. Accordingly, alopecia (baldness) also includes a deficiency in terminal hairs.

One non-drug treatment for alopecia is hair transplantation. Plugs of skin containing hair are transplanted from areas of the scalp where hair is growing to bald areas. This approach can be reasonably successful; however it is costly, time-consuming and painful. Other non-drug related approaches to treating alopecia include ultra-violet radiation, massage, psychiatric treatment and exercise therapy. None of these approaches, however, have been generally accepted as effective. Even such things as revascularization surgery or acupuncture have shown little, if any, effect.

SUMMARY OF THE INVENTION

Compositions and methods are disclosed herein for topical application of an effective amount of at least one penetration enhancer and cyclopentane heptanoic acid, 2-cycloalkyl or arylalkyl compound represented by the formula I:

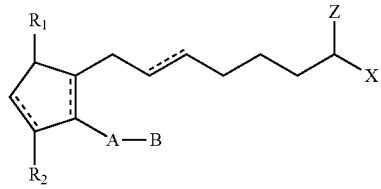

wherein the dashed bonds represent the presence or absence of a double bond which can be in the cis or trans configuration, A is an alkylene or alkenylene radical having from two to six carbon atoms, which radical can be interrupted by one or more oxo radicals and substituted with one or more hydroxy, oxo, alkyloxy or alkylcarboxy groups wherein the alkyl radical comprises from one to six carbon atoms; B is a cycloalkyl radical having from three to seven carbon atoms, or an aryl radical, selected from the group consisting of hydrogen, a lower alkyl radical having from four to ten carbon atoms wherein the heteroatom is selected from the group consisting of nitrogen, oxygen and sulfur atoms; X is $-N(R_4)_2$ wherein $R_4$ is selected from the group consisting of hydrogen, a lower alkyl radical having from one to six carbon atoms,

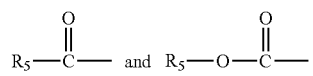

wherein $R_5$ is a lower alkyl radical having from one to six carbon atoms; Z is $=O$; one of $R_1$ and $R_2$ is $=O$, $-OH$ or a $-O(CO)R_6$ group, and the other one is $-OH$ or $-O(CO)R_6$, or $R_1$ is $=O$ and $R_2$ is H, wherein $R_6$ is a saturated or unsaturated acyclic hydrocarbon group having from 1 to about 20 carbon atoms, or $-(CH_2)mR_7$ wherein m is 0 or an integer of from 1 to 10, and $R_7$ is cycloalkyl radical, having from three to seven carbon atoms, or a hydrocarbyl aryl or heteroaryl radical, as defined above in free form or a pharmaceutically acceptable salt thereof, in association with a penetration enhancer in particular formulations adapted for topical application to mammalian skin.

In one embodiment, the cyclopentane heptanoic acid, 2-cycloalkyl or arylalkyl compound represented by the formula I is the compound bimatoprost.

Another embodiment includes a composition comprising bimatoprost at a concentration of about 0.001-1.5% w/w, from 0.01-1.0% w/w, from 0.02-1.0% w/w, 0.03 to about 1.0% w/w, 0.03 to 0.9% w/w, 0.04 to 0.8% w/w, 0.05-0.7% w/w, 0.06%-0.6% w/w, 0.07%-0.5% w/w, 0.08-0.4% w/w, 0.09-0.3% w/w, 0.1% w/w, 0.2% w/w, 0.3% w/w, 0.4% w/w, 0.5% w/w, 0.6% w/w, 0.7% w/w, 0.8% w/w, 0.9% w/w and 1.0% w/w. The following excipients may be also be included: Carbomer at a concentration of about 0.05-1.0% w/w; base at a concentration of about 0.01 to about 2.0% w/w; ethanol at a concentration of about 10 to about 90% w/w; glycerin at a concentration of about 1.0 to about 20% w/w; diethylene glycol monoethyl ether at a concentration of about 1.0 to about 50% w/w; polysorbate 20 at a concentration of about 0.1 to about 5.0% w/w; polysorbate 40 at a concentration of about 0.1 to about 5.0% w/w; polysorbate 60 at a concentration of about 0.1 to about 5.0% w/w; polysorbate 80 at a concentration of about 0.1 to about 5.0% w/w; PPG-5 ceteth-20 at a concentration of about 0.1 to about 5.0% w/w; oleic acid at a concentration of about 0.1 to about 5.0% w/w; isostearyl isostearate at a concentration of about 0.1 to about 10% w/w; isopropyl myristate at a concentration of about 0.1 to about 10% w/w; dipropylene glycol dimethyl ether at a concentration of about 1 to about 50% w/w; diethylene glycol at a concentration of about 1 to about 50% w/w; dipropylene glycol at a concentration of about 1 to about 50% w/w; caprylic/capric at a concentration of about 0.1 to about 10% w/w; benzyl alcohol at a concentration of about 0.1 to about 2.0% w/w; silicone at a concentration of about 0.1 to about 10% w/w; and/or water at a concentration of about 0 to about 90% w/w.

Another embodiment includes a composition comprising bimatoprost at about 0.1% w/w; carbomer at about 0.10% w/w; NaOH at about 0.035% w/w; ethanol at about 15.0% w/w; diethylene glycol monoethyl ether at about 10.0% w/w; and water at about 74.8% w/w.

Another embodiment includes a composition comprising bimatoprost at about 0.1% w/w; carbomer at about 0.15% w/w; triethylamine (TEA) at about 0.22% w/w; ethanol at about 15.0% w/w; diethylene glycol monoethyl ether at about 10.0% w/w; polysorbate 20 at about 4.0% w/w; and water at about 70.5% w/w.

Another embodiment includes a composition comprising bimatoprost at about 0.1% w/w; carbomer at about 0.125% w/w; TEA at about 0.18% w/w; ethanol at about 30.0% w/w; diethylene glycol monoethyl ether at about 20.0% w/w; and water at about 49.59% w/w.

Another embodiment includes a composition comprising bimatoprost at about 0.1% w/w; carbomer at about 0.10% w/w; TEA at about 0.15% w/w; ethanol at about 30.0% w/w; propylene glycol at about 20% w/w; and water at about 49.7% w/w.

Another embodiment includes a composition comprising bimatoprost at about 0.1% w/w; carbomer at about 0.20% w/w; TEA at about 0.22% w/w; ethanol at about 60.0% w/w; glycerin at about 5.0% w/w; and water at about 34.48% w/w.

Another embodiment includes a composition comprising bimatoprost at about 0.1% w/w; carbomer at about 0.25% w/w; TEA at about 0.38% w/w; ethanol at about 60.0% w/w; polysorbate 20 at about 4.0% w/w; and water at about 35.27% w/w.

Another embodiment includes a composition comprising bimatoprost at about 0.1% w/w; carbomer at about 0.25% w/w; TEA at about 0.38% w/w; ethanol at about 50.0% w/w; diethylene glycol monoethyl ether at about 10% w/w; polysorbate 20 at about 4.0% w/w; and water at about 35.27% w/w.

The compositions were manufactured using the following general procedure. Non-aqueous components (e.g. bimatoprost, ethanol, glycols) were combined in a beaker and stirred using a propeller type overhead mixer until the solution was clear. Water was added to the non-aqueous mixture followed by the addition of the thickening agent. Upon dispersion of the thickening agent, a base was added to neutralize the polymer and thicken the solution into a gel.

DETAILED DESCRIPTION

Bimatoprost is a moderately soluble compound intended for topical delivery to the skin to stimulate hair growth. Hair growth includes, without limitation, stimulating the conversion of vellus hair to growth as terminal hair as well as increasing the rate of growth of terminal hair. Embodiments disclosed herein provide formulations of bimatoprost and similar compounds with penetration enhancers. These penetration enhancers facilitate active component penetration and/or maintenance at their site of action in the skin. Formulations disclosed herein can be self-preserved or contain an antimicrobial agent such as benzyl alcohol.

In accordance with embodiments disclosed herein, active components are represented by

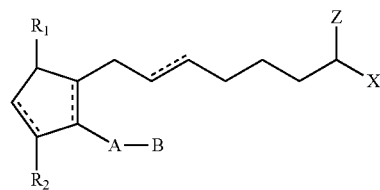

The active components are provided in particular formulations that include penetration enhancers. Some examples of representative compounds useful in the practice of embodiments disclosed herein include the compounds shown in Table 1:

TABLE 1

Representative Compounds cyclopentane heptenamide-5-cis-2-(3α-hydroxy-5-phenyl-1-trans-pentenyl)-3,5-dihydroxy, [1$_\alpha$,2$_\beta$,3$_\alpha$,5$_\alpha$] cyclopentane N,N-dimethylheptenamide-5-cis-2-(3α-hydroxy-5-phenyl-1-trans-penten-yl)-3,5-dihydroxy, [1$_\alpha$,2$_\beta$,3$_\alpha$,5$_\alpha$]
cyclopentane heptenylamide-5-cis-2-(3α-hydroxy-4-meta-chlorophenoxy-1-trans-pent-enyl)-3,5-dihydroxy, [1$_\alpha$,2$_\beta$,3$_\alpha$,5$_\alpha$]
cyclopentane heptenylamide-5-cis-2-(3α-hydroxy-4-trifluoromethylphenoxy-1-trans-pentenyl)-3,5-dihydroxy, [1$_\alpha$,2$_\beta$,3$_\alpha$,5$_\alpha$]
cyclopentane N-isopropyl heptenamide-5-cis-2-(3α-hydroxy-5-phenyl-1-trans-pentenyl)-3,5-dihydroxy, [1$_\alpha$,2$_\beta$,3$_\alpha$,5$_\alpha$]

TABLE 1-continued

Representative Compounds cyclopentane N-ethyl heptenamide-5-cis-2-(3α-hydroxy-5-phenyl-1-trans-pentenyl)-3,5-dihydroxy, [1α,2β,3α,5α]
cyclopentane N-methyl heptenamide-5-cis-2-(3α-hydroxy-5-phenyl-1-trans-pentenyl)-3,5-dihydroxy, [1α,2β,3α,5α]
cyclopentane heptenamide-5-cis-2-(3α-hydroxy-4-meta-chlorophenoxy-1-trans-butenyl)-3,5-dihydroxy, [1α,2β,3α,5α]

In one embodiment, the compound is a cyclopentane heptanoic acid, 2-(phenyl alkyl or phenyloxyalkyl) represented by the formula II:

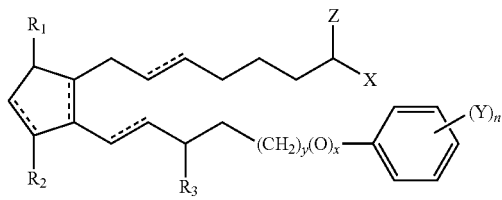

wherein y is 0 or 1, x is 0 or 1 and x and y are not both 1, Y is selected from the group consisting of alkyl, halo, e.g. fluoro, chloro, etc., nitro, amino, thiol, hydroxy, alkyloxy, alkylcarboxy, halo substituted alkyl wherein said alkyl radical comprises from one to six carbon atoms, etc. and n is 0 or an integer of from 1 to 3 and $R_3$ is =O, —OH or —O(CO)$R_6$ wherein $R_6$ is as defined above or a pharmaceutically acceptable salt thereof.

In another embodiment, the compound is a compound of formula III:

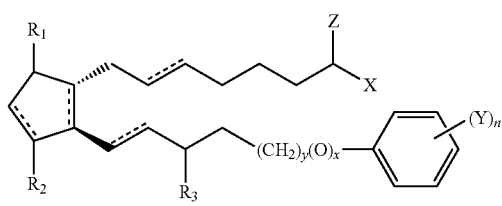

wherein hatched lines indicate α configuration, solid triangles are used to indicate β configuration. In another embodiment, y is 1 and x is 0 and $R_1$, $R_2$ and $R_3$ are hydroxy.

One exemplary compound is cyclopentane N-ethyl heptanamide-5-cis-2-(3α-hydroxy-5-phenyl-1-trans-pentenyl)-3,5-dihydroxy, [1α,2β,3α,5α], also known as bimatoprost and sold under the name of LUMIGAN® by Allergan, Inc., California, USA. This compound has the following structure:

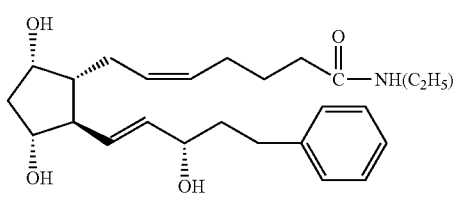

The synthesis of the above compounds has been disclosed in U.S. Pat. No. 5,607,978 which is incorporated by reference in its entirety.

Effective amounts of the active compounds can be determined by one of ordinary skill in the art but will vary depending on the compound employed, frequency of application and desired result. The compound will generally range from about $1 \times 1^{-7}$ to about 50% w/w of the composition, in one embodiment from about 0.001 to about 50% w/w of the composition and in another embodiment from about 0.1 to about 30% w/w of the composition. Ranges of within about 10-50% w/w; about 20-50% w/w; about 30-40% w/w and about 35% are also included.

The pharmaceutical formulations disclosed herein can include one or more penetration enhancers. The phrase "penetration enhancers" includes any agent that facilitates the transfer of active components to their site of action or maintains them at their site of action. Non-limiting examples of classes of appropriate penetration enhancers include alcohols, glycols, fatty acids, ethers, esters, occlusive agents and surface active agents. Representative examples of these classes are provided below.

Alcohols include, without limitation, ethanol, propanol, N-propanol, isopropanol, butyl alcohol, octanol, benzyl alcohol and acetyl alcohol, in one embodiment, as described in U.S. Pat. No. 5,789,244, the entire contents of which are incorporated by reference herein. Fatty alcohols include, for example, stearyl alcohol and oleyl alcohol.

Glycols include, without limitation, glycerine, propyleneglycol, polyethyleneglycol and other low molecular weight glycols such as glycerol and thioglycerol.

Fatty acids, esters and ethers include, without limitation, oleic acid, palmitoleic acid, straight chain $C_4$-$C_{20}$ saturated monocarboxylic and dicarboxylic acids, octanoic and decanoic acids, methyl laurate, ethyl oleate, polyethylene glycol monolaurate, propylene glycol monolaurate, propylene glycol dilaurate, glycerol monolaurate, glycerol monooleate, isopropyl n-decanoate, octyldodecyl myristate, diethylene glycol monoethyl ether, diethylene glycol monomethyl ether and compounds wherein a $C_2$-$C_4$ alkane diol or triol is substituted with one or two fatty ether substituents.

Occlusive agents include, without limitation, silicones, mineral oils and greases, long chain acids, animal fats and greases, vegetable fats and greases, water insoluble polymers, paraffin, paraffin oil, liquid paraffin, petrolatum, liquid petrolatum, white petrolatum, yellow petrolatum, microcrystalline wax and ceresin.

Surface active agents include without limitation, polysorbate 20, 40, 60 and 80, TWEEN® (20, 40, 60, 80), POLOXAMER® (231, 182, 184), sodium dodecyl sulfate (SDS), lecithin, lysolecithin, nonylphenoxypolyoxyethylene, lysophosphatidylcholine, polyethylenglycol 400, polyoxyethylene ethers, polyglycol ether surfactants, DMSO, sodium laurate, sodium lauryl sulfate, cetyltrimethylammonium bromide, and benzalkonium chloride.

Additional penetration enhancers will be known to those of ordinary skill in the art of topical drug delivery, and/or are described in the pertinent texts and literature.

Embodiments disclosed herein can also include viscosity increasing agents. Appropriate agents include, without limitation, methylcellulose, polyvinyl alcohol, polyvinyl pyrrolidone, hyaluronic acid and chondroitin sulfate.

Certain embodiments disclosed herein can include preservatives including, without limitation, benzyl alcohol, benzalkonium chloride, chlorhexidine, chlorobutanol, methyl-, propyl-, or butyl-parahydroxybenzoic acids, phenylmercuric salts including, without limitation, nitrate, chloride, acetate, and borate and betain.

Various other additives may be included in the compositions of the present invention in addition to those identified above. These include, but are not limited to, antioxidants, astringents, perfumes, emollients, pigments, dyes, humectants, propellants, and sunscreen agents, as well as other classes of materials whose presence may be cosmetically, medicinally or otherwise desirable. The compositions and formulations may also be taken in conjunction with minoxidil and propecia.

Compositions can also be formulated as "slow-releasing" formulations so that the activity of active components is sustained for a longer period of time between treatments.

While particular embodiments disclosed herein can include each of the components discussed above, other particular embodiments can be required to be "substantially free" of one or more of these components in various combinations. "Substantially free", as used herein, means that the component is not added to a formulation and cannot be present in any amount greater than about 1% w/w.

While not limiting the scope of express exclusion of the preceding paragraph, particular embodiments disclosed herein can be substantially free of one or more of bimatoprost, carbomer, NaOH (s), TEA, ethanol, glycerin, diethylene glycol, monoethyl ether, propylene glycol, polysorbate 20, polysorbate 40, polysorbate 60, polysorbate 80, PPG-5 ceteth-20, oleic acid, isostearyl isostearate, isopropyl myristate, dipropylene glycol dimethyl ether, diethylene glycol, dipropylene glycol, triglycerides, caprylic/capric, benzyl alcohol, silicone and water.

All components of formulations described herein will be included in amounts that are dermatologically-acceptable. As used herein, "dermatologically-acceptable" means that the compositions or components thereof are suitable for use in contact with human skin without undue toxicity, incompatibility, instability, allergic response, and the like. As used in herein as applied to active agents and excipients, the term "about" refers to variations in concentrations which are considered to be bioequivalent.

Embodiments disclosed herein find application in mammalian species, including both humans and animals. In humans, the compounds of embodiments disclosed herein can be applied without limitation, to the scalp, face, beard, head, pubic area, upper lip, eyebrows, and eyelids. The compositions of the present inventions may be used for treating various hair loss disorders including but not limited to alopecia areata, telogen effluvium, anagen effluvium, cicatricial alopecia and scarring alopecia; hair shaft abnormalities such as trichorrexis nodosa, loose anagen syndrome, trichotillomania and traction alopecia; infectious hair disorders such as tiniea capitis, sebohorreic dermatitis, and follicullitus of the scalp; genetic disorders such as androgenetic alopecia and patients undergoing hair loss due to chemotherapy, hormonal imbalance (e.g., thyroid conditions such as hypothyroidism and hyperthyroidism, pregnancy, child birth, discontinuation of birth control pills and changes in menstrual cycle), fungal infection of the scalp such as ringworm, medicines which cause hair loss such as anticoagulants, medicine for gout, depression, high blood pressure and certain heart medications. The formulations of the present invention may be used to treat hair loss related to other disease such as diabetes, lupus, and poor nutrition, mental and physical stress such as due to surgery, illness and high fever. Environmental factors and chemicals used in hair treatment (dying, tinting and bleaching).

In animals raised for their pelts, e.g., mink, the formulations can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The compositions and methods of the present invention may be applied to patients suffering from hair loss or in healthy patients simply wanting to increase hair growth in any part of the body.

The compositions disclosed herein are formulated for topical administration. The term "topical administration" as used herein includes applying a formulation as described herein to the outer skin or hair. The application will generally occur at or near the area of desired hair growth.

Accordingly, appropriate formulation or composition types include, without limitation, solutions, gels, ointments, foams, films, liniments, creams, shampoos, lotions, pastes, jellies, sprays and aerosols. Such formulation types can be applied in swaths, patches, applicators or through the use of impregnated dressings depending on the situation and part of the body to be treated.

Typically, the formulations described herein will be applied repeatedly for a sustained period of time to the part of the body to be treated. In particular embodiments, formulations disclosed herein can include one or more applications daily, one or more applications weekly, one or more applications monthly or one or more applications yearly for a period of treatment of at least one day, at least one week, at least one month, at least one year or until the treatment has achieved or achieved and maintained a desired result.

Formulations described herein will be administered in safe and effective amounts. As used herein, "safe and effective amounts" include an amount sufficient so that the composition provides the desired hair growth stimulation effect at a reasonable benefit/risk ratio attendant with any medical treatment. Within the scope of sound medical judgment, the amount of active components used can vary with the particular condition being treated, the severity of the condition, the cause of the condition, the duration of the treatment, the specific active component employed, its concentration, the specific vehicle utilized, the general health of the patient, the tolerance of the patient to various effects of the administration, other drugs being administered to the patient, and like factors within the specific knowledge and expertise of the patient or attending physician.

For daily administration, an appropriate dose can include, without limitation, about 0.1 ng to about 100 mg, about 1 ng to about 10 mg per day or in another embodiment about 10 ng to about 1 mg per day.

Non-limiting examples of some components with their appropriate concentration ranges and function are provided in Table 1 below. Particular examples of non-limiting formulations or compositions are provided in Table 2.

TABLE 1

Example Components with Function and Concentration Ranges

| Ingredient | Function | Composition (% w/w) |
|---|---|---|
| bimatoprost | Active | 0.03-1.0 |
| carbomer | Thickener | 0.05-1.0 |
| base | Neutralizing Agent | 0.01-2.0 |
| ethanol | Penetration enhancers | 10-90 |
| glycerin | | 1.0-20 |
| diethylene glycol monoethyl ether | | 1.0-50 |
| propylene glycol | | 1-50 |
| polysorbate 20 | | 0.1-5.0 |
| polysorbate 40 | | 0.1-5.0 |
| polysorbate 60 | | 0.1-5.0 |
| polysorbate 80 | | 0.1-5.0 |
| PPG-5 ceteth-20 | | 0.1-5.0 |
| oleic acid | | 0.1-5.0 |
| isostearyl isostearate | | 0.1-10 |
| isopropyl myristate | | 0.1-10 |
| dipropylene glycol dimethyl ether | | 1-50 |
| diethylene glycol | | 1-50 |
| dipropylene glycol | | 1-50 |
| caprylic/capric triglycerides | | 0.1-10 |
| benzyl alcohol | Preservative | 0.1-2.0 |
| silicone | Occlusive Agent | 0.1-10 |
| water | Vehicle | 0-90 |

TABLE 2

Example Compositions

| Ingredient | Function | Composition (% w/w) | | | | | | |
|---|---|---|---|---|---|---|---|---|
| bimatoprost | Active | 0.1 | 0.1 | 0.1 | 0.1 | 0.1 | 0.1 | 0.1 |
| carbomer | Thickener | 0.10 | 0.15 | 0.125 | 0.10 | 0.20 | 0.25 | 0.25 |
| NaOH (s) | Neutralizing Agent | 0.035 | | | | | | |
| TEA | Neutralizing Agent | | 0.22 | 0.18 | 0.15 | 0.22 | 0.38 | 0.38 |
| ethanol | Penetration enhancers | 15.0 | 15.0 | 30.0 | 30.0 | 60.0 | 60.0 | 50.0 |
| glycerin | | | | | | 5.0 | | |
| diethylene glycol monoethyl ether | | 10.0 | 10.0 | 20.0 | | | | 10 |
| propylene glycol | | | | | 20 | | | |
| polysorbate 20 | | | 4.0 | | | | 4.0 | 4.0 |
| water | Vehicle | 74.8 | 70.5 | 49.595 | 49.7 | 34.48 | 35.27 | 35.27 |

TABLE 3

Bimatoprost Scalp Hair Growth Topical Gel Formulations

| Ingredient (% w/w) | Function | Bimatoprost 0.03% (Propylene Glycol) Solution | Bimatoprost 0.1% (Propylene Glycol) Solution | Bimatoprost 0.3% (Propylene Glycol) Solution | Bimatoprost 0.2% (Propylene Glycol) Solution |
|---|---|---|---|---|---|
| Bimatoprost | Active | 0.03 | 0.1 | 0.3 | 0.2 |
| Propylene glycol | Penetration enhancer | 10.0 | 10.0 | 10.0 | 10.0 |
| Diethylene glycol monoethyl ether | | 10.0 | 10.0 | 10.0 | 10.0 |
| Ethyl alcohol | | 30.0 | 30.0 | 30.0 | 30.0 |
| Glycerin | | 2.0 | 2.0 | 2.0 | 2.0 |
| Carbomer (Ultrez 10) | Thickener | 0.15 | 0.15 | 0.15 | 0.15 |
| Triethanolamine | Neutralizing agent | 0.16 | 0.16 | 0.16 | 0.16 |
| Purified water | Vehicle | 47.66 | 47.59 | 47.39 | 47.49 |

Example I

Preparations of Bimatoprost Scalp Hair Growth Gel Compositions

Ethyl alcohol is weighed into a suitable media jar equipped for mixing, bimatoprost is then added to the ethyl alcohol and stirred at moderate speed until bimatoprost is dissolved. Into separate mixing tank water for injection, glycerin, diethylene glycol monoethyl ether, and propylene glycol are added and mixed until the solvents are dispersed. Ethyl alcohol/bimatoprost solution is then added into the water mixture and mixed until the components are homogenously mixed (about 5 minutes of mixing). To the above mixture the carbomer thickener is added and mixed until well dispersed, once dispersed a base is added to thicken the solution into a gel. Representative formulations made according to the method above are shown in Table 3 below.

Example II

In Vivo Treatment

A study is initiated to systematically evaluate the appearance of hair on the scalp and eyebrows who are administered bimatoprost gel formulations as in Table 3. The study involves 10 subjects, 5 male, 5 female, average age 70 years, (ranging from 50-94 years). Each subject is treated daily by the topical application of bimatoprost by the 0.3% w/w bimatoprost formulation of Table 3.

The study is limited to subjects who have administered bimatoprost for more than 3 months. The mean duration of exposure to the 0.3% w/w bimatoprost gel formulation prior to assessing the parameter of hair or eyebrow growth between the control and study eye is 129 days (range 90-254 days). Observations are made under high magnification at a slit lamp biomicroscope. Documentation of differences between the control and treatment areas is accomplished using a camera specially adapted for use with a slit lamp biomicroscope.

The Results of the Observations Will Be as Follows:

Length of hair and eyebrows: Increased length of hair in both groups is regularly observed. The difference in length varies from approximately 10% to as much as 30%.

Number of hairs and eyebrows: Increased numbers of hairs are observed on the scalp and eyebrows of each patient. The difference in number of hair and eyebrows varies from approximately 5% to as much as 30%. Whether statistically significant or not, bimatoprost with a penetration enhancer will provide better and/or faster results than bimatoprost without a penetration enhancer.

The foregoing observations will establish that 0.03% w/w bimatoprost composition penetrates skin and grows hair.

Example III

Topical Cream

A topical 0.2% w/w bimatoprost cream is prepared as follows: Tegacid and spermaceti are melted together at a temperature of 70-80° C. Methylparaben is dissolved in about 500 gm of water and propylene glycol, polysorbate 80, bimatoprost and a penetration enhancer are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example IV

Topical Cream

A 0.1% w/w bimatoprost topical cream is prepared as follows: Tegacid and spermaceti are melted together at a temperature of 70-80° C. Methylparaben is dissolved in water and propylene glycol, polysorbate 80, bimatoprost and a penetration enhancer are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example V

Topical Ointment

An Ointment Containing 2.0% w/w Bimatoprost is Prepared as Follows:

White petrolatum and wool fat are melted, strained and liquid petrolatum is added thereto. Bimatoprost, a penetration enhancer, zinc oxide, and calamine are added to the remaining liquid petrolatum and the mixture milled until the powders are finely divided and uniformly dispersed. The mixture is stirred into the white petrolatum, melted and cooled with stirring until the ointment congeals. In other variants, the zinc oxide and/or calamine can be omitted such that the formulation is substantially free of the zinc oxide or calamine.

Example VI

Ointment

An ointment containing 5% w/w bimatoprost and a penetration enhancer is prepared by adding the active compound to light liquid petrolatum. White petrolatum is melted together with wool fat, strained, and the temperature adjusted to 45-50° C. The liquid petrolatum slurry is added and the ointment stirred until congealed. The ointment can be packaged in 30 gm tubes.

Example VII

Spray Formulation

An aqueous spray formulation containing 0.03%, w/w bimatoprost and a penetration enhancer are prepared as follows. Bimatoprost and a penetration enhancer are dissolved in water and the resulting solution is sterilized by filtration. The solution is aseptically filled into sterile containers with a spray nozzle for application on top of the head. The formulation is as follows:

TABLE 4

Bimatoprost Spray Formulation of Example VII

| Ingredient (% w/w) | Function | Spray formulation |
| --- | --- | --- |
| Bimatoprost | Active | 0.03 |
| Propylene glycol | Penetration enhancer | 5 |
| Diethylene glycol monoethyl ether | | 5 |
| Ethyl alcohol | | 15 |
| Light mineral oil | | — |
| Ceteareth 12 | | — |
| Glycerin | | 1 |
| Carbomer (Ultrez 10) | Thickener | — |
| Triethanolamine | Neutralizing agent | — |
| Purified water | Vehicle | 24 |
| Hydrofluoro carbon, hydrocarbon propellant, $CO_2$, or, Nitrogen | Propellant | 49.97 |

Example VIII

Lotion

A sample of bimatoprost and a penetration enhancer is dissolved in the vehicle of N-methyl pyrrolidone and propylene glycol to make a 0.5% w/w bimatoprost lotion for application to the scalp or other parts of the body for growing hair.

Example IX

Aerosol

An aerosol containing approximately 0.1% w/w bimatoprost and a penetration enhancer is prepared by dissolving the bimatoprost and a penetration enhancer in absolute alcohol. The resulting solution is filtered to remove particles and lint. This solution is chilled to about −30° C. A chilled mixture of dichlorodifluoromethane and dichlorotetrafluoroethane is then added to the solution. Thirteen ml plastic-coated amber bottles can be cold filled with 11.5 gm each of the resulting solution and capped. The aerosol may be sprayed onto the scalp or other parts of the body to grow hair.

Example X

Topical Foam Formulation

A 0.1% w/w bimatoprost topical foam formulation is prepared as follows: Methylparaben is dissolved in about 500 gm of water and propylene glycol, polysorbate 80, bimatoprost and a penetration enhancer are added in turn, maintaining a temperature of 75-80° C. The methylparaben mixture is added slowly to Tegacid and spermaceti, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

An alternative foam formulation prepared in a similar manner as taught in Example X in Table V is as follows:

| Ingredient (% w/w) | Function | Foam formulation |
|---|---|---|
| Bimatoprost | Active | 0.03 |
| Propylene glycol | Penetration enhancer | — |
| Diethylene glycol monoethyl ether | | 5 |
| Ethyl alcohol | | 10 |
| Light mineral oil | | 6 |
| Ceteareth 12 | | 5 |
| Glycerin | | — |
| Carbomer (Ultrez 10) | Thickener | — |

Example XI

Dusting Powder

A powder of the compound bimatoprost and a penetration enhancer is prepared by mixing in dry form with talcum powder at a weight/weight ratio of 1:1:10.

Example XII

Related Compounds

Following the procedures of the preceding Examples, compositions are similarly prepared substituting an equimolar amount of a compound of Table 1 for the bimatoprost disclosed in the preceding Examples.

Unless otherwise indicated, all numbers expressing quantities of ingredients, properties such as molecular weight, reaction conditions, etc. used in the specification and claims are to be understood as being modified in all instances by the term "about." "About" refers to variations in concentrations of excipients and types of excipients which are considered to be bioequivalent according to the FDA and other regulatory authorities.

Example XIII

A 44 year old Caucasian male undergoing hair loss due to alopecia areata applies once daily before sleeping the 0.1% w/w bimatoprost composition of Table 3 for a period of 6 months. After 3 months of application, the subject will notice new hair growth where there previously had been none and darkening of the follicles of old hair. Observations of new hair growth are made under high magnification at the slit lamp biomicroscope and by computer assisted image analysis. Documentation of differences between the control and treatment areas is accomplished using a camera specially adapted for use with the slit lamp biomicroscope.

Example XIV

A 37 year old Hispanic male suffering from male pattern baldness due to androgenetic alopecia applies the 0.2% w/w bimatoprost composition of Table 3 twice daily in areas where hair is noticeably thinning. After 63 days of application, increased growth of hair will be noticed as will be new hair growth as measured by high magnification at the slit lamp biomicroscope and by computer assisted image analysis. After satisfactory levels of hair growth are observed, the patient applies the 0.2% w/w bimatoprost composition only twice a week.

Example XV

A 29 year old Caucasian healthy female wishes to have fuller hair and more hair growth even though no disease or hair loss condition has been diagnosed by doctors. The patient will apply the 0.3% w/w bimatoprost composition of Table 3 once daily until more hair growth is observed after approximately three months of use. The patient continues to apply the composition once a week to maintain the increased hair growth.

Example XVI

A 35 year old African American male diagnosed with follicular degeneration syndrome and associated hair loss will apply the 0.03% w/w bimatoprost composition of Table 3. The composition will be applied twice daily, once in the morning after showering and once in the evening. After 46 days of application, increased hair growth will be noticed and easing of the symptoms of follicular degeneration syndrome. The patient continues application for another 6 months.

What is claimed is:

1. A composition for topical application to human skin, the composition comprising:
    0.01% to 5% w/w bimatoprost in free form or a pharmaceutically acceptable salt thereof; and,
    a penetration enhancer comprising a combination of
        a group comprising ethanol, propylene glycol, and diethylene glycol monoethyl ether, and
        an effective amount of at least two compounds selected from the group consisting of glycerol monooleate, oleic acid, and benzyl alcohol.

2. The composition of claim 1, wherein the penetration enhancer comprises ethanol, propylene glycol, diethylene glycol monoethyl ether, glycerol monooleate, oleic acid, and benzyl alcohol.

3. The composition of claim 1, wherein the composition comprises 5% w/w bimatoprost.

4. The composition of claim 1, wherein the composition comprises 1% w/w bimatoprost.

5. The composition of claim 1, wherein the composition comprises 0.3% w/w bimatoprost.

6. The composition of claim 1, wherein the composition comprises 0.1% w/w bimatoprost.

7. The composition of claim 1, wherein the composition is in the form of one selected from the group consisting of solutions, gels, ointments, foams, films, liniments, creams, shampoos, lotions, pastes, jellies, sprays, and aerosols.

8. The composition of claim 1, wherein the composition is in the form of a gel.

9. The composition of claim 1, wherein the composition is in the form of a solution.

10. The composition of claim 1, wherein the composition is in the form of an ointment.

* * * * *